(12) United States Patent
Sinha et al.

(10) Patent No.: US 8,084,438 B2
(45) Date of Patent: Dec. 27, 2011

(54) COMPOSITIONS AND METHODS OF SPHINGOSINE KINASE INHIBITORS IN RADIATION THERAPY OF VARIOUS CANCERS

(75) Inventors: Uttam K. Sinha, Los Angeles, CA (US); Rizwan Masood, Walnut, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/772,833

(22) Filed: May 3, 2010

(65) Prior Publication Data
US 2010/0331393 A1    Dec. 30, 2010

Related U.S. Application Data

(63) Continuation of application No. 11/948,981, filed on Nov. 30, 2007, now abandoned.

(60) Provisional application No. 60/868,046, filed on Nov. 30, 2006.

(51) Int. Cl.
*C12N 15/11* (2006.01)
*A61N 5/00* (2006.01)
*A61N 5/10* (2006.01)

(52) U.S. Cl. ............. 514/44 A; 536/24.5; 600/1; 378/65

(58) Field of Classification Search .................. None
See application file for complete search history.

(56) References Cited

U.S. PATENT DOCUMENTS
2004/0171037 A1 * 9/2004 Li et al. ............................. 435/6

OTHER PUBLICATIONS

GenBank Accession BC011432 (Nov. 19, 2003).*
Samsel et al (The Prostate 58: 382-393, 2004).*
Validation of an anti-sphingosine-1 phosphate antibody as a potential therapeutic in reducing growth, invasion, and angiogenesis in multiple tumor lineages (Cancer Cell 2006;9:225-38) by Barbara Visentin, et al.
Sphingosine Kinase Mediates Vascular Endothelial Growth Factor-Induced Activation of Ras and Mitogen-Activated Protein Kinases (Mole) (Cell. Bio 2002;22:77587768) by Xiaodong Shu, et al.
Sphingosine Kinase-1 as a Chemotherapy Sensor in Prostate Adenocarcinoma Cell and Mouse Models (Cancer Res. 2005;65:11667-75) by Dimitri Pchejetski, et al.
Sphingosine kinase 1 is up-regulated in colon carcinogenesis. (FASEB J. 2006; 20:386-8) by Toshihiko Kawamori, et al.
Discovery and Evaluation of Inhibitors of Human Sphingosine Kinase. (Cancer Res. 2003;63;5962-9) by Kevin J. French,et al.
N,N-Dimethylsphingosine Is a Potent Competitive Inhibitor of Sphingosine Kinase but Not of Protein Kinase C: Modulation of Cellular Levels of Sphingosine 1-Phosphate and Ceramide (Biochemistry. 1998;37:12892-8) by Lisa C. Edsall, et al.
Sphingosine Enhances Apoptosis of Radiation-resistant Prostate Cancer Cells (Cancer Res. 2000 Aug. 15;60 (16):4468-74) by Victor E. Nava, et al.
PCT International Search Report mailed Sep. 10, 2008 based on PCT/US2007/086057.

* cited by examiner

*Primary Examiner* — Richard Schnizer
(74) *Attorney, Agent, or Firm* — DLA Piper LLP (US)

(57) ABSTRACT

The present invention relates to Sphingosine kinase inhibitors that are useful for treating various cancers. The invention further relates to compositions and methods of SPK inhibitors, including siRNAs, which specifically block gene expression of SPK and potentiates the effect of radiation in the treatment of various cancers.

16 Claims, 12 Drawing Sheets

COMPOSITIONS AND METHODS OF SPHINGOSINE KINASE INHIBITORS IN RADIATION THERAPY OF VARIOUS CANCERS

The present application is a continuation of Ser. No. 11/948,981, filed Nov. 30, 2007 now abandoned, which claims the benefit of the filing date of U.S. Provisional Application No. 60/868,046, filed Nov. 30, 2006, the disclosure of which is incorporated herein by reference in its entirety.

FIELD OF THE INVENTION

The present invention relates in general to treatment of diseases. More specifically, the invention provides compositions comprising sphingosine kinase inhibitors and methods of using the compositions in radiation therapy for the treatment of various cancers.

BACKGROUND OF THE INVENTION

There are millions of patients worldwide afflicted with cancer who are treated with radiation therapy. Radiation therapy is used as a primary therapy or in combination with surgery and/or chemotherapy and/or hormone therapy. Most common cancer types may be treated with radiation therapy in some way. The precise treatment or radiation dose depends upon the tumor type, location, stage, as well as the general health of the patient. In most cases, radiation therapy is given to patients for two to six weeks at a total dose of 50 Gy to 70Gy. High doses of radiation is required to kill all the cancer cells, but the radiation injures both the tumor cells as well as normal tissues that are in its path and treatment causes many side effects. Side effects include soreness, diarrhea, nausea, edema, infertility, fatigue, fibrosis, hair loss, dryness of mouth, or damage to salivary glands. In some cases, radiation itself can lead to the formation of cancer. Repetitive use high doses of radiation is limited because the chances of damage to vital organs such as the spinal cord increases as exposure to radiation increases. Thus, there is a need for therapeutic agents which can effectively reduce the dose of radiation required to treat cancer cells so that side effects may be minimized or eliminated and radiation therapy may be repeated as necessary.

Sphingolipids such as ceramide and sphingosine (SPH) are a class of apoptosis regulators in cancer cells. Ceramide inhibits proliferation and promotes apoptosis (10), while sphingosine-1-phosphate (S1P) is a key tumor-promoting lipid, responsible for tumor cell proliferation, migration and invasion (1). S1P is synthesized by phosphorylation of SPH. However, the formation of SW antagonizes the formation of ceramide. The opposing directions between the formation of ceramide and S1P is referred to as the "sphingolipid rheostat" and plays a pivotal role in regulating tumor growth (10) (FIG. 1). The levels of ceramide and S1P are regulated by sphingosine kinase-1 (SPK-1), whose overexpression has been shown to inhibit apoptosis (10). Studies have also shown that elevated levels of S1P and increased SPK-1 activity in cancers is due to the overexpression of SPH (2,3), while the reduction of SPK1 levels in cancer cells results in apoptosis of the cancer cells (10, 15).

SPK-1 activity has been shown to be upregulated in many types of cancers including various squamous cell carcinomas (SCC) such as head and neck, lung, bladder, ovary, prostate, and skin cancers. Likewise, cell lines from various types of cancers including the human breast cancer (MCF-7) (6-8); intestinal tumors (9); prostate adenocarcinomas (10); colon cancers (11); lung cancers (12); erytholeukemias (13); and bladder tumors (14) also exhibit SPK-1 overexpression.

French et. al. used various cancer cells and cell lines including human breast cells and breast, colon, lung, ovary, stomach, uterus, kidney and rectum tumors from patients, to demonstrate that SPK mRNA is over-expressed in cancer as compared to normal tissue in the surrounding area of the same organ (15). French used a chemical library of 16,000 compounds to screen for compounds that inhibited SPK overexpression. Four compounds were discovered, but not all of these compounds were specific for SPK inhibition, as some compounds inhibited other human kinases.

Nava, et al., showed a relationship between SPK-1 and resistance to irradiation in prostate cancer cell lines. SPK1 activity in radioresistant LNCaP cells were not affected by gamma-irradiation, but SPK1 levels of radiosensitive TSU cells were noticeably inhibited by gamma-irradiation. Radioresistant LNCaP cells were however, sensitized to gamma-irradiation when treated with TNF-alpha, which is known to decrease SPK1 levels (23).

Other pharmacological agents that have been shown to reduce the levels of SPK in tumor cells include phenoxodiol (16); dimethylsphingosine (DMS) (18); docetaxel and camptothecin (10); agents derived from marine bacterium B-5354 (19) and fungus (20); and sphingoside analogs (17). However, these pharmacological agents exhibit moderate levels of anti-tumor activity or exhibit toxicity that makes the use of pharmacological inhibitors undesirable. Thus, there is a need for inhibitors that are effective at inhibiting SPK overexpression, without producing undesirable side effects.

Small interfering RNAs (siRNAs) have been shown to specifically "knock out" or "silence" the gene of specific proteins and enzymes and are effective at inhibiting the overexpression of SPK without the toxicities and other undesirable side effects associated with the use of pharmacological inhibitors.

siRNAs have been shown to reduce SPK-1 activity and induce apoptosis in MCF-7 cells (21) and decrease cell viability in PC-3 cells (22).

SUMMARY OF THE INVENTION

In one embodiment, the invention relates to SPK inhibitors that specifically block SPK overexpression in a variety of cancer cells.

In another embodiment, the invention relates to SPK inhibitors that silences or knocks out the gene responsible for SPK over-expression and induces apoptosis.

In a further embodiment, the invention relates to SPK inhibitors that silence or knock out the gene responsible for SPK over-expression potentiate the effect of radiation in a variety of cancer cells.

In a related embodiment, the invention relates to compositions comprising SPK inhibitors that specifically blocks SPK over-expression in a variety of cancer cells.

In another embodiment, the invention relates to compositions comprising SPK inhibitors that silences or knocks out the gene responsible for SPK over-expression and induces apoptosis in a variety of cancer cells.

In yet another embodiment, the invention relates to compositions comprising SPK inhibitors that silence or knock out the gene responsible for SPK over-expression potentiate the effect of radiation in a variety of cancer cells.

In a related embodiment, the invention relates to methods using SPK inhibitors to knock out or silence the gene responsible for SPK over-expression in cancer cells. The method comprises transfecting cancer cells with SPK inhibitors and determining the amount of SPK expression. If SPK expression in cancer cells that have been transfected with SPK inhibitor decreases more than the SPK expression of cancer cells that have not been transfected with SPK inhibitor, then the SPK inhibitor has silenced or knocked out SPK gene expression.

In accordance with another embodiment, the invention relates to a method of using SPK inhibitors to potentiate the effect of radiation. The method comprises irradiating cancer cell lines that have been transfected with and without SPK inhibitors. If the cell viability percentage of irradiated SPK transfected cancer cells decreases more than the cell viability of irradiated cancer cells that have not been transfected with SPK inhibitor, then the SPK inhibitor has reduced the amount of radiation needed to decrease cancer cell viability and the effect of radiation has been potentiated.

In a closely related embodiment, the invention relates to a method of using SPK inhibitors to potentiate the effect of radiation in vivo. The method comprises injecting a mammal with cancer cells that have been transfected with and without SPK inhibitors and irradiating said mammal. If the tumor volume of the animal treated with the SPK inhibitor decreases more than the tumor volume of the mammal treated without SPK inhibitor, then the SPK inhibitor has reduced the amount of radiation needed to decrease tumor size in vivo and the effect of radiation has been potentiated.

Within one aspect, the present invention provides SPK inhibitors comprising siRNA. More specifically the siRNA comprises 19-25 oligonucleotide bases.

Within one further aspect, the present invention provides SPK inhibitors comprising double stranded siRNA (HNB-001) with a sense sequence of 5'-GGG CAA GGC UCU GCA GCU CTT-3' (SEQ ID NO: 1) and antisense sequence of 5'-GAG CUG CAG AGC CUU GCC CTT-3' (SEQ ID NO: 2).

Within another aspect, the present invention provides SPK inhibitors comprising double stranded siRNA (HNB-002) with a sense sequence of 5'-GGG CAA GGC CUU GCA GCU CTT-3' (SEQ ID NO: 3) and antisense sequence of 5'-GAG CUG CAA GGC CUU GCC CTT-3' (SEQ ID NO: 4).

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
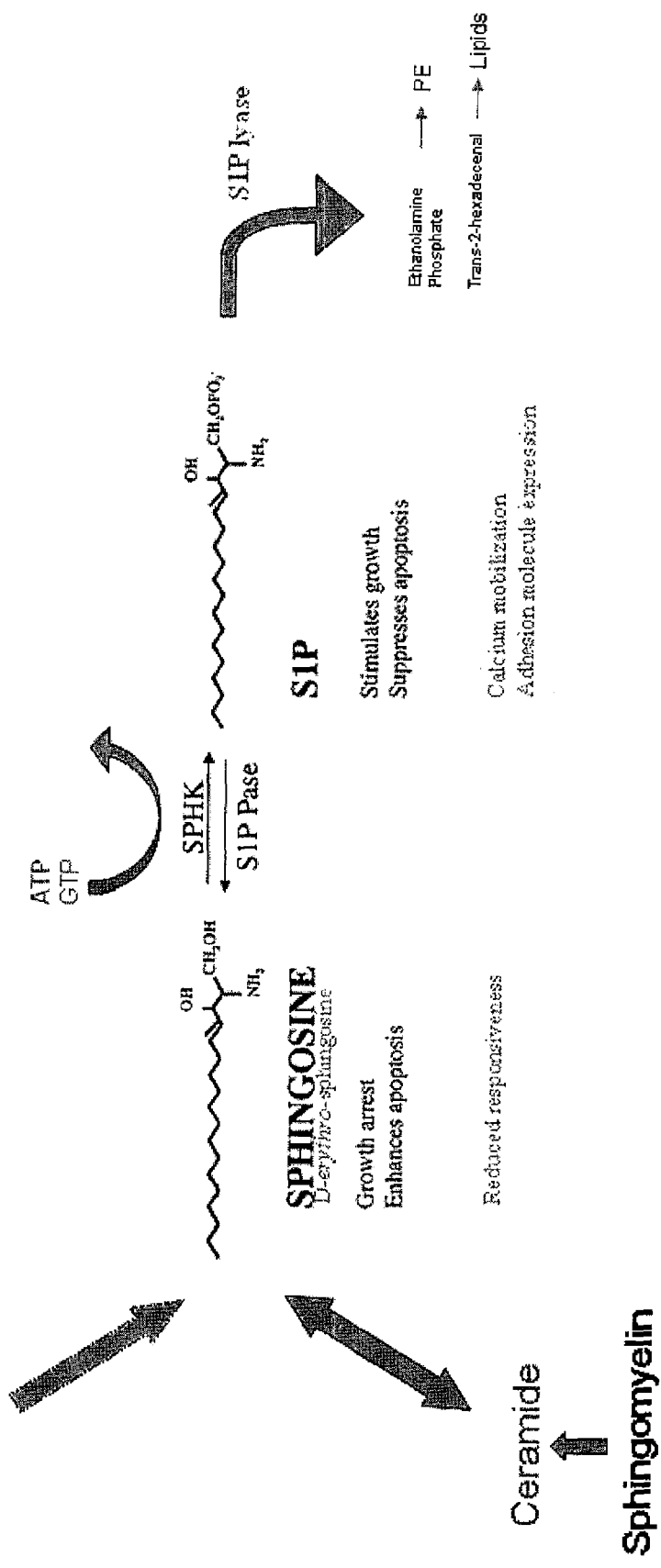
FIG. 1. Schematic representation of the synthesis of Ceramide, Sphingosine (SPH) and Sphingosine-1-Phosphate (S-1-P).

It is well known that various types of cancer cells (i.e., head and neck squamous cell carcinoma, leukemia, breast, colon, lung, ovary, stomach, uterus, kidney, rectum, prostate, bladder, skin, ovary, brain, etc.) overexpress SPK (10-45), and that apoptosis of these cancer cells may be induced by inhibiting SPK overexpression (15).

The present invention provides compositions and methods of inhibitors that block SPK over-expression in a variety of cancers. More specifically the present invention provides siRNA inhibitors that are SPK specific and potentiate the effect of radiation in cancer cells.

As used herein the terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, brain cancer, bladder cancer, prostate cancer, colon cancer, intestinal cancer, squamous cell cancer, lung cancer, stomach cancer, pancreatic cancer, cervical cancer, ovarian cancer, liver cancer, skin cancer, colorectal cancer, endometrial carcinoma, salivary gland carcinoma, kidney cancer, thyroid cancer, various types of head and neck cancer, and the like.

The term "overexpression," as used herein refers to overexpression of a gene and/or its encoded protein in a cell, such as a cancer cell. A cancer cell that "overexpresses" a protein is one that has significantly higher levels of that protein compared to a noncancerous cell of the same tissue type.

The phrase "induces apoptosis" refers to the ability of a SPK inhibitor to induce programmed cell death by inhibiting SPK overexpression by silencing or knocking out SPK gene expression.

"Potentiate the effect of radiation" refers to the ability to render tumor cells more susceptible to treatment by radiation. Tumor cells that have been potentiated to the effect of radiation show a significantly higher decrease in cell viability or tumor size when compared to normal cells that have been exposed to the same dosage of radiation.

"Therapeutic agent" is an agent that may directly decrease the pathology of tumor cells, render the tumor cells more susceptible to treatment by other therapeutic agents, e.g., radiation and/or chemotherapy, or reduces the percentage of cells overexpressing SPK.

"Mammal" for purposes of treatment refers to any animal classified as a mammal, including humans, mice, primates, rabbits, rats, cats, dogs, and the like.

To practice the methods relating to silencing or knocking out gene expression, a cancer cell line or cancer cells are obtained from a tissue containing cancer. The cancer cells are transfected with a SPK inhibitor and the expression level of the SPK gene in the cells are determined and compared to a control level. A control level may be the expression level of the SPK gene in a cancer cell that has not been transfected with a SPK inhibitor, such as green fluorescent protein siRNA (GFP siRNA), or a normal cell from a tissue of the same body location. If the expression level of the SPK gene in the test sample is lower than the control level, the SPK inhibitor has knocked out or silenced the gene responsible for SPK overexpression.

To practice the methods relating to SPK inhibitors that potentiate the effect of radiation in cancer cells, a cancer cell line or cancer cells are obtained from a tissue containing cancer. The cancer cells are transfected with a SPK inhibitor, irradiated and the cell viability is determined and compared to a control level. A control level may be the cell viability of cancer cells that were irradiated and not transfected with a SPK inhibitor, cells that were irradiated and transfected with lipofectamine, cells that were transfected with a SPK inhibitor such as GFP siRNA, but was not irradiated. If the cell viability of the test sample is lower than the control levels, the SPK inhibitor has potentiated the effect radiation on cancer cells.

To select SPK specific inhibitors, several mouse and human SPK-1 phosphorothioate antisense oligonucleotides were tested in head and neck squamous cell lines. Phosphothionate-modified oligonucleotides were synthesized and purified (Core facilities at the USC/Norris Comprehensive Cancer Center, Microchemical Core Facility Los Angeles, Calif.). SPK-1 antisense oligonucleotides from different regions of the mouse SPK-1 and human SPK-1 coding region were synthesized. The sequence of each oligonucleotide are as follows:

```
                                        (SEQ ID NO: 5)
hSPK-1-1:   5'-GAG CTG CAA GGC CTT GCC CTT- 3'

(SEQ ID NO: 6)
hSPK-1-2:   5'-AGG CCG CTC CAT GAG CCC GTT- 3'

(SEQ ID NO: 7)
hSPK-1-3:   5'-GTT GGT CAG GAG GTC TTC ATT- 3'

(SEQ ID NO: 8)
hSPK-1-4:   5'-GGT GTC TTG GAA CCC ACT CTT- 3'

(SEQ ID NO: 9)
hSPK-1-5:   5'-ATA CTC CAT ATG CCT GCC CTT- 3'

(SEQ ID NO: 10)
hSPK-1-6:   5'-CGG CCT CGC TAA CCA TCA ATT- 3'

(SEQ ID NO: 11)
mSPK-1-1:   5'-GAG CTG CAG AGC CTT GCC CTT- 3'

(SEQ ID NO: 12)
mSPK-1-2:   5'-TCC GTT CGG TGA GTA TCA GTT- 3'

(SEQ ID NO: 13)
mSPK-1-3:   5'-CAC CAG CTC CCT GGC ATG GTT- 3'

(SEQ ID NO: 14)
mSPK-1-4:   5'-GTT GAT GAG CAG GTC TTC ATT- 3'
```

-continued

```
                                        (SEQ ID NO: 15)
mSPK-1-5    5'-GCA CAA CAG CAG TGT GCA GTT- 3'

(SEQ ID NO: 16)
mSPK-1-6    5'-CCA GGT ATG GAC AGT CAA GTT- 3'
```

Six of each, mouse and human antisense oligonucleotides (1-6) corresponding to different regions of SPK-1 cDNAs were tested for activity against HNSCC cell growth. Only one of the six antisense oligonucleotides (hSPK-1-2) showed potent inhibitory activity. The hSPK-1-1 oligonucleotide had minimal inhibitory effect on HNSCC cells and the hSPK-1-3, hSPK-1-4, and hSPK-1-5 antisense oligonucleotides also showed some inhibitory activity in HNSCC cells.

The SPK inhibitor HNB-001 showed potent inhibitory activity against HNSCC cell growth. It corresponds to a SPK-1 coding region in mouse and comprises the sense sequence: 5-GGG CAA GGC UCU GCA GCU CUU-3' (SEQ ID NO: 1) and antisense sequence: 5'-GAG CUG CAG AGC CUU GCC CTT-3' (SEQ ID NO: 2). Likewise, HNB-002 also showed potent inhibitory activity against HNSCC cell growth. It corresponds to a SPK-1 coding region in humans, and comprises the sense sequence: 5'-GGG CAA GGC CUU GCA GCU CTT-3' (SEQ ID NO: 3) and antisense sequence: 5'-GAG CUG CAA GGC CUU GCC CTT-3' (SEQ ID NO: 4).

SPK inhibitors of the present invention may comprise siRNA. More specifically the siRNA may be 19-25 oligonucleotide bases long.

Control siRNA may be green fluorescence protein siRNA (GFP siRNA) comprising the sense sequence: 5'-CGG CCA CAA GUU CAG CGU GUC dTdT-3' (SEQ ID NO: 17) and antisense sequence: 5-GAC ACG CUG AAC UUG UGG CCG dTdT-3' (SEQ ID NO: 18).

Gene expression levels may be detected and quantified at the mRNA or protein level using a number of means well known in the art. To detect mRNAs or measure mRNA levels, cells in biological samples (e.g., tissues and body fluids) may be lysed and the mRNA in the lysates or in RNA purified or semi-purified from the lysates detected or quantified by any of a variety of methods familiar to those in the art. Such methods include, without limitation, hybridization assays using detectably labeled gene-specific DNA or RNA probes and quantitative or semi-quantitative RT-PCR (e.g., real-time PCR) methodologies using appropriate gene-specific oligonucleotide primers. Alternatively, quantitative or semi-quantitative in situ hybridization assays can be carried out using, for example, unlysed tissues or cell suspensions, and detectably (e.g., fluorescently or enzyme-) labeled DNA or RNA probes. Additional methods for quantifying mRNA levels include RNA protection assay (RPA), cDNA and oligonucleotide microarrays, and colorimetric probe based assays.

Methods for detecting proteins or measuring protein levels in biological samples are also known in the art. Many such methods employ antibodies (e.g., monoclonal or polyclonal antibodies) that bind specifically to target proteins. In such assays, an antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein measuring assays (e.g., ELISA or Western blot) can be applied to body fluids or to lysates of test cells, and others (e.g., immunohistological methods or fluorescence flow cytometry) applied to unlysed tissues or cell suspensions. Methods of measuring the amount of a label depend on the nature of the label and are known in the art. Appropriate labels include, without limitation, radionuclides (e.g., 125I, 131I, 35S, 3H, or 32P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

Therapeutic agents are formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

In one embodiment, the therapeutic agents are prepared with carriers that will protect the compounds against rapid elimination from the body, such as a controlled release formulation, including implants and microencapsulated delivery systems. Therapeutic agents, may also comprise siRNAs conjugated to cationic polypeptides, amphipathic compounds, polycations, liposomes or PEGlyated liposomes. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It is advantageous to formulate oral or parenteral compositions in dosage unit form for ease of administration and uniformity of dosage. "Dosage unit form," as used herein, refers to physically discrete units suited as unitary dosages for the subject to be treated, each unit containing a predetermined quantity of an active compound calculated to produce the desired therapeutic effect in association with the required pharmaceutical carrier.

The dosage required for treating a subject depends on the choice of the route of administration, the nature of the formulation, the nature of the subject's illness, the subject's size, weight, surface area, age, and sex, other drugs being administered, and the judgment of the attending physician. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

Example

Immunohistochemistry Staining for SPK Expression

Figure 2:
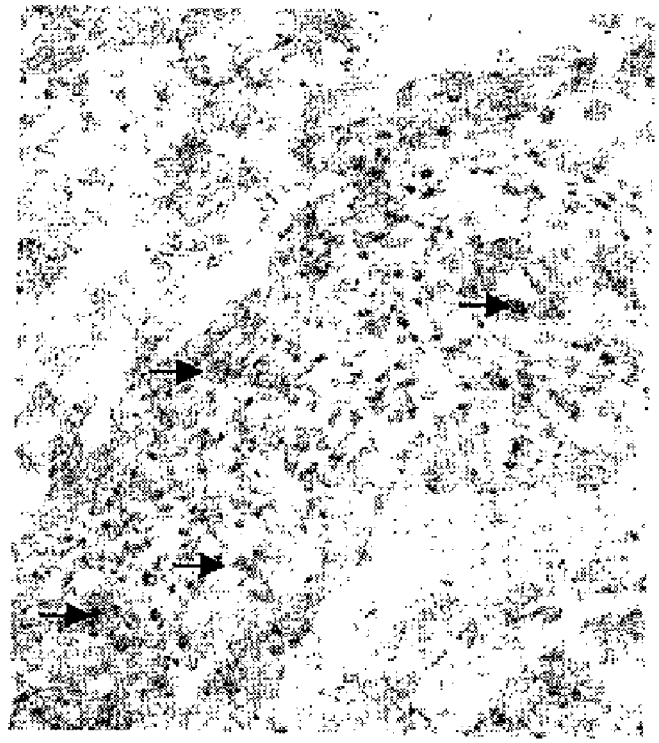
FIG. 2. Representative Immunohistochemistry (IHC) staining of head and neck tumor tissue for SPK expression. The left panel shows an absence of SPK staining in normal tissue. The arrows in the right panel show positive staining for SPK in tumor regions.
Figure 2:

Head and neck tumor biopsy samples and adjacent normal tissue were paraffin-embedded according to the methods of Atkins et. al., who demonstrated a preferred method for detection of protein with specific antibody (21). Sections were studied by immunohistochemistry within one week of cutting the sections. Cut sections were placed on slides, rinsed twice in PBS and preincubated with blocking buffer (0.2% Triton-X100, 1% BSA in PBS) for 20 min, followed by incubation at 4° C. for 16 hr with SPK as a primary antibody that was added to the blocking buffer. After washing three times in PBS, sections were incubated with HRP-conjugated secondary antibody for 1 hr at 25° C. Peroxidase activity was revealed by the diaminobenzidine (Sigma) cytochemical reaction. Sections were counterstained with 0.12% methylene blue or H&E and mounted in IMMU-MOUNT (Shandon, Astmoor UK). SPK was expressed in the tumor regions only, as there was no SPK staining in the stroma and normal tissues (FIG. 2). Likewise, a metastatic tumor site in the lymph node showed positive staining while the normal lymph node was negative (data not shown).

Example 2

Western Blotting for SPK Expression in Tumor Tissue

Figure 3:
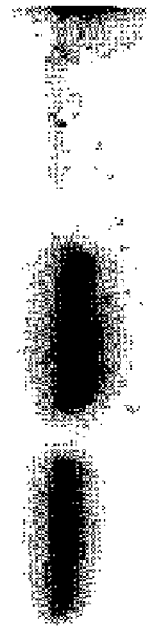
FIG. 3. Representative western blot for SPK-1 expression in HNSCC primary tissues and metastases. Western blots of HNSCC tissue lysates consisting of lymph node biopsies (LN), tumor (T), and normal tissue (N) were prepared using a SPK specific antibody. The tumor and lymph node tissue show positive SPK staining, while the normal tissue shows minimal SPK staining.
Figure 3:
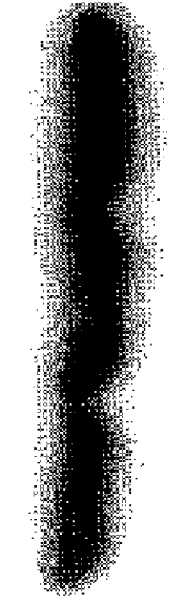
Figure 3:
Figure 3:

Western blots of tissue from primary tumor, lymph node metastases, and normal tissue were carried out to determine the relative levels of SPK expression in those sites. Normal tissues adjacent to tumors, tumor, and lymph nodes were collected from several patients. SPK expression was observed in each of the tumor samples. Similarly, all tumor-positive lymph nodes showed SPK expression that was equal to or slightly greater than the primary tumor (FIG. 3). No or minimal expression was observed in the normal tissue that was a adjacent to the tumor. Quantitative analysis by stage and lymph node status showed that SPK levels were substantially higher in stage III/IV compared to stage I/II.

Western blotting was performed by adding tissues to 0.5 ml of cold lysis buffer (50 mM Tris, pH 8, 150 mM NaCl, 1% Triton X-100, 0.5 mM EDTA, containing Halt Protease Inhibitor cocktail [Pierce, Rockford Ill.]) and homogenizing them on ice using a PowerGen 125 homogenizer (Fisher Scientific). Homogenized samples were transferred to 1.7 ml microcentrifuge tubes and centrifugated at 10,000×g for 10 min at 4° C. to clear the lysates. Protein extracts were gently removed and put into fresh tubes. Total protein was determined by Dc colorimetric assay (BioRad, Richmond, Calif.). Protein samples (25 µg protein) were fractionated on 4-20% Tris-glycine polyacrylamide gels and transferred to polyvinylidene difluoride (PVDF) membrane (Bio-Rad) by electroblotting. Membranes were blocked with 5% non-fat milk prior to incubation with primary SPK antibody at 4° C., for 16 hr. Secondary antibody (1:100,000 dilution) conjugated with horseradish peroxidase was applied for 1 hr at 25° C. The membranes were developed using the SuperSignal West Femto Maximum sensitivity chemiluminescent substrate (Pierce, Rockford, Ill.) according to the manufacturer's instructions. The same membranes were stripped and re-probed with β-actin and the chemiluminescent signal was quantitated using BioRad QuantityOne software analysis and specific proteins normalized to β-actin in each sample.

Example 3

Western Blotting for SPK-1 Expression in siRNA Treated Cells

Figure 4:
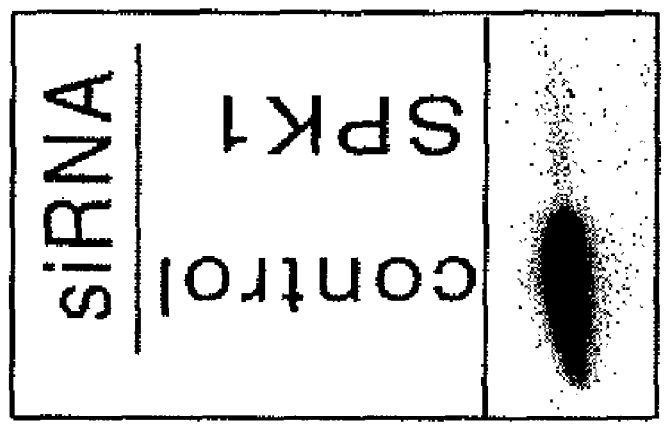
FIG. 4. Representative western blot for SPK-1 expression in siRNA treated cells. (Left)) SCC cells treated with siRNA (SPK1 lane) and without siRNA (control lane). (Right) Schematic showing a decrease in the concentration of S1P and increase the concentration of ceramide when SPK mRNA is inhibited by siRNA.
Figure 4:
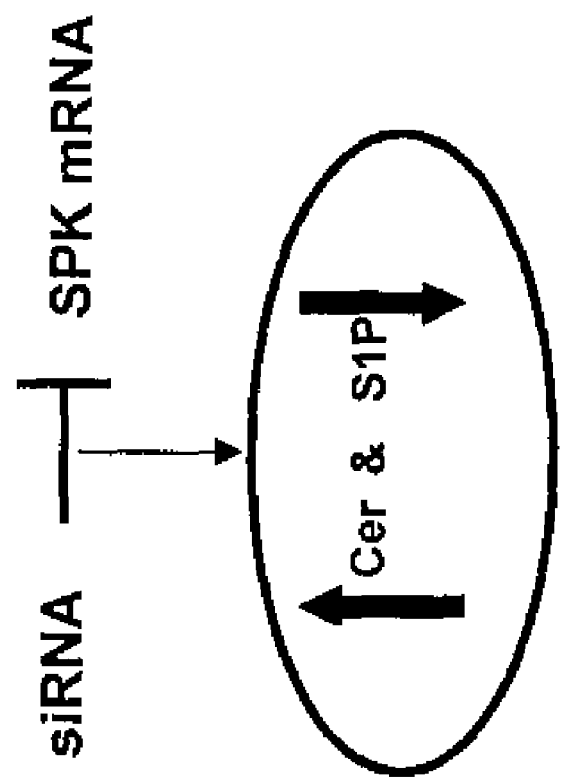

SCC cell lines (SCC-04, SCC-15, SCC-25 and SCC-71) from ATCC were seeded on six well plates. Lipofectamine™ 2000 was used according to the manufacturer's instructions to introduce siRNA (10-100 nM of HNB-001) into the SCC cells. Control SCC cells were transfected with lipofectamine only. Four hours post-transfection, the cells were returned to growth media (DMEM/10% FCS). Three days after transfection, the cells were harvested and washed once with cold PBS. The cell pellet was lysed in lysis buffer and the extracted protein was tested for SPK expression by Western Blotting. SPK expression in SCC cells treated with siRNA was reduced by 95% as compared to the control (FIG. 4, left image). This clearly demonstrates that, the siRNA inhibitor has silenced or knocked out the gene responsible for SPK expression. In addition, the sphingolipid rheostat teaches that the concentration of S1P is decreased while the concentration of ceramide is increased (FIG. 4, right image).

Example 4

Viability of SCC-71 Cells Exposed to Radiation

Figure 5:
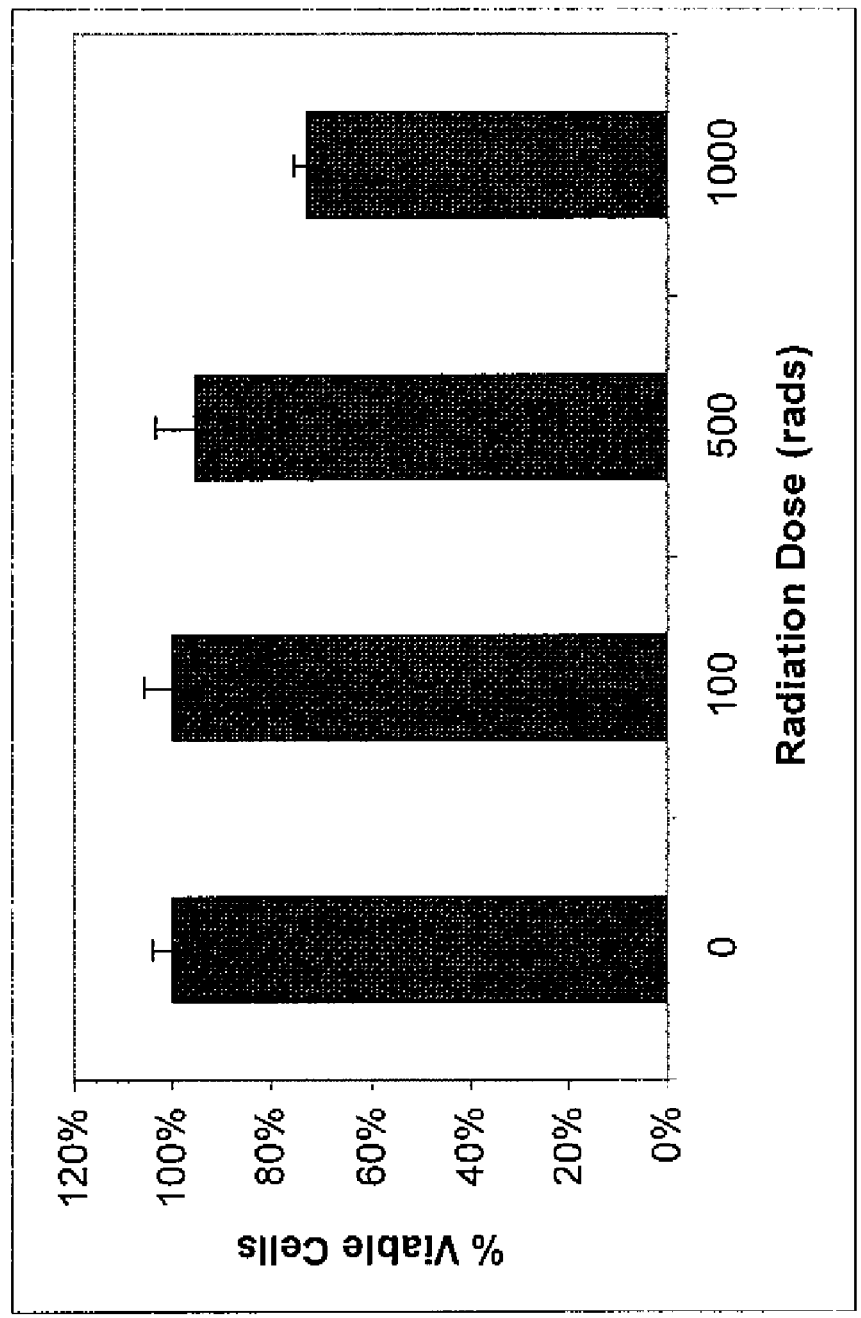
FIG. 5. Graph of viable SCC-71 cells as a function of radiation doses FIG. 6. Graph of viable SCC-71 cells as a function of siRNA concentration and/or radiation dosage.

SCC-71 cells were seeded in T25 flasks. Lipofectamine™ 2000 was used according to the manufacturer's instructions to introduce siRNA (10-100 nM HNB-001) into the cells. Four hours post-transfection, the cells were returned to growth media (DMEM/10% FCS) and two days later the media was changed and the cells were irradiated with 0-1000 rads of Caesium-137 (Cs-137 irradiator source, gammacell 40). Forty-eight hours after irradiation, cell viability was determined using trypan blue staining. Radiation doses of 0 to 500 rads had no affect on cell viability, but there was about a 20% decrease in viability for cells irradiated at 1000 rads (FIG. 5).

Example 5

Viability of siRNA Transfected SCC-71 Cells Exposed to Radiation

Figure 6:
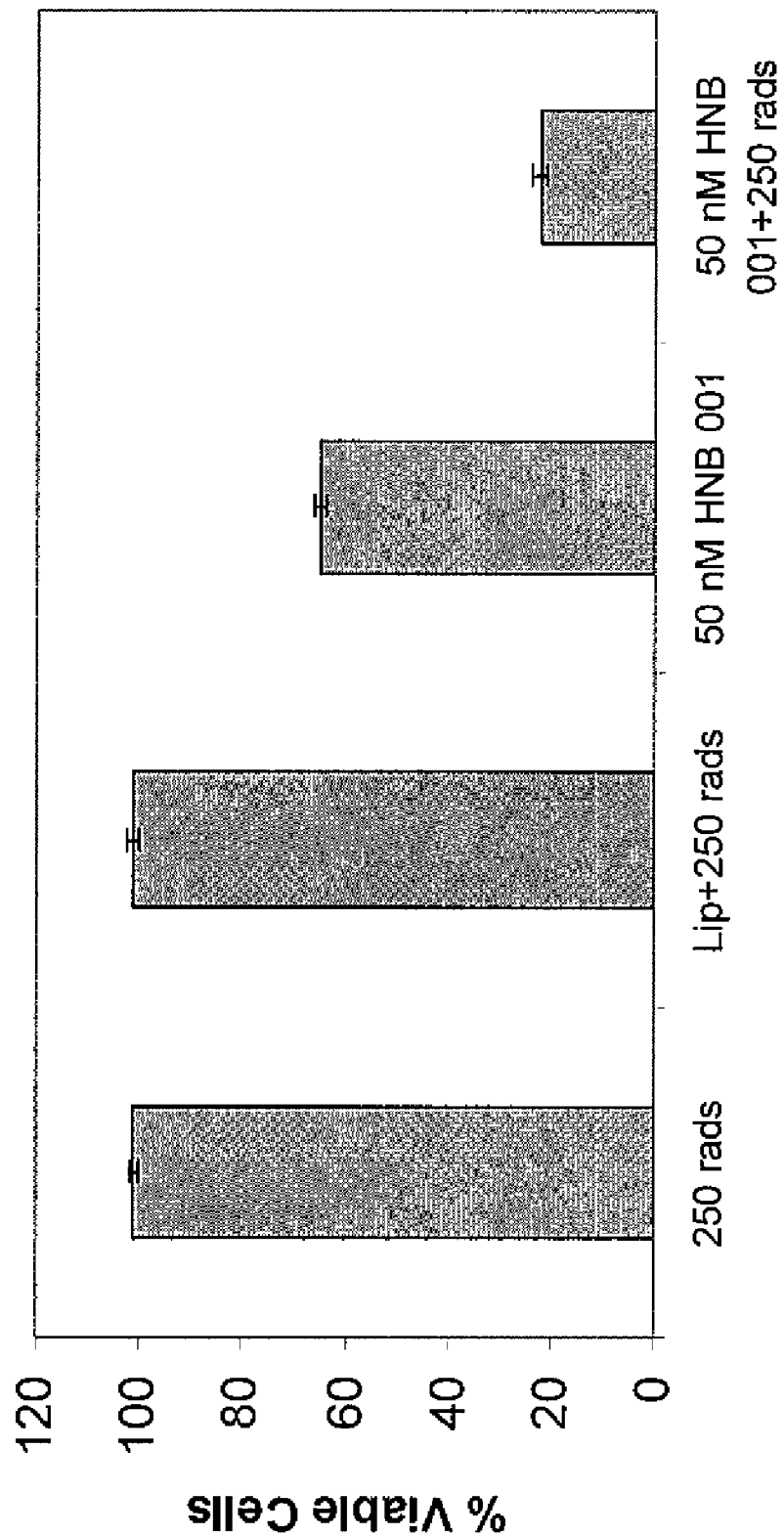

Four different groups of SCC-71 cells were compared to determine the viability of siRNA (50 nM HNB-001) transfected cells after exposure to radiation. All cells were irradiated at 250 rads, a dosage where cell toxicity was not previously observed (see example 4). Group I, consisted of irradiated SCC-71 cells; group II consisted of irradiated, lipofectamine transfected cells; group III consisted of unirradiated, siRNA transfected cells; and group IV consisted of irradiated siRNA transfected cells. Forty-eight hours after irradiation, cell viability was determined using trypan blue staining. Radiation exposure did not affect the cell viability of the SCC-71 cells in groups I and II (FIG. 6). However, there was about a 35% reduction in cell viability of the unirradiated, siRNA transfected cells (group III). Surprisingly there was about an 80% decrease in the viability of the irradiated cells that were transfected with siRNA (group IV). These results clearly demonstrates that siRNA potentiates the effect of radiation.

Example 6

Figure 7:
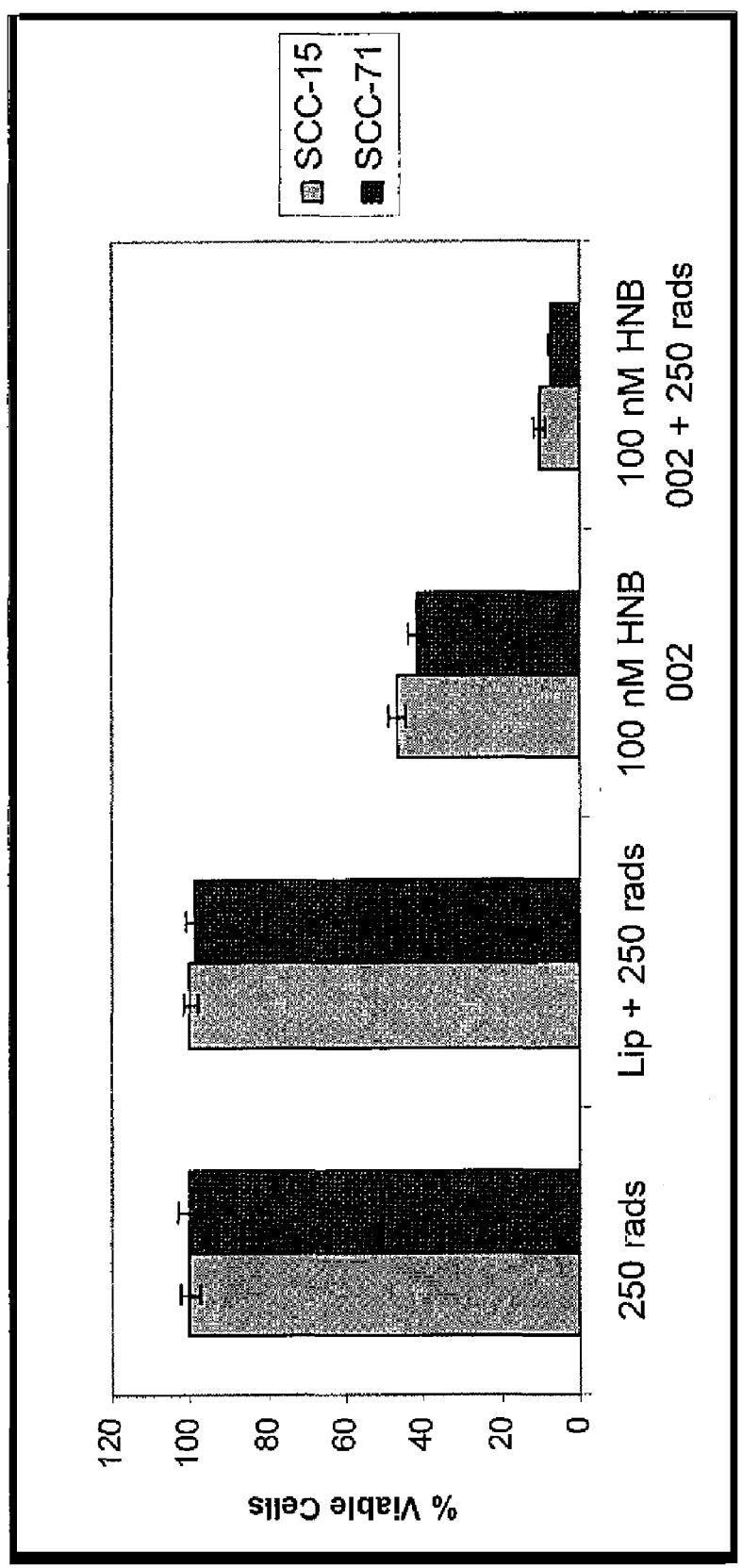
FIG. 7. Graph of viable SCC-71 and SCC-15 cells as a function of siRNA concentration and/or radiation dosage.

Comparison of the Viability of SCC-71 and SCC-15 siRNA Transfected Cells Exposed to Radiation Four different groups of both SCC-71 and SCC-15 cells were compared to determine the viability of siRNA (100 nM HNB-002) transfected cells after exposure to radiation. The groups in this experiment were similar to Example 5. The results show that cell viability of both the SCC-15 and SCC-71 cells in groups I and II were unaffected by exposure to radiation (FIG. 7). However, over a 50%© decrease in cell viability was observed for both SCC-71 and -15 cells in group III (unirradiated, siRNA transfected cells). Surprisingly there was about a 90% decrease in the viability of the irradiated cells that were transfected with siRNA (group IV).

Example 7

Viability of siRNA Transfected MCF-7 Cells Exposed to Radiation

Figure 8:
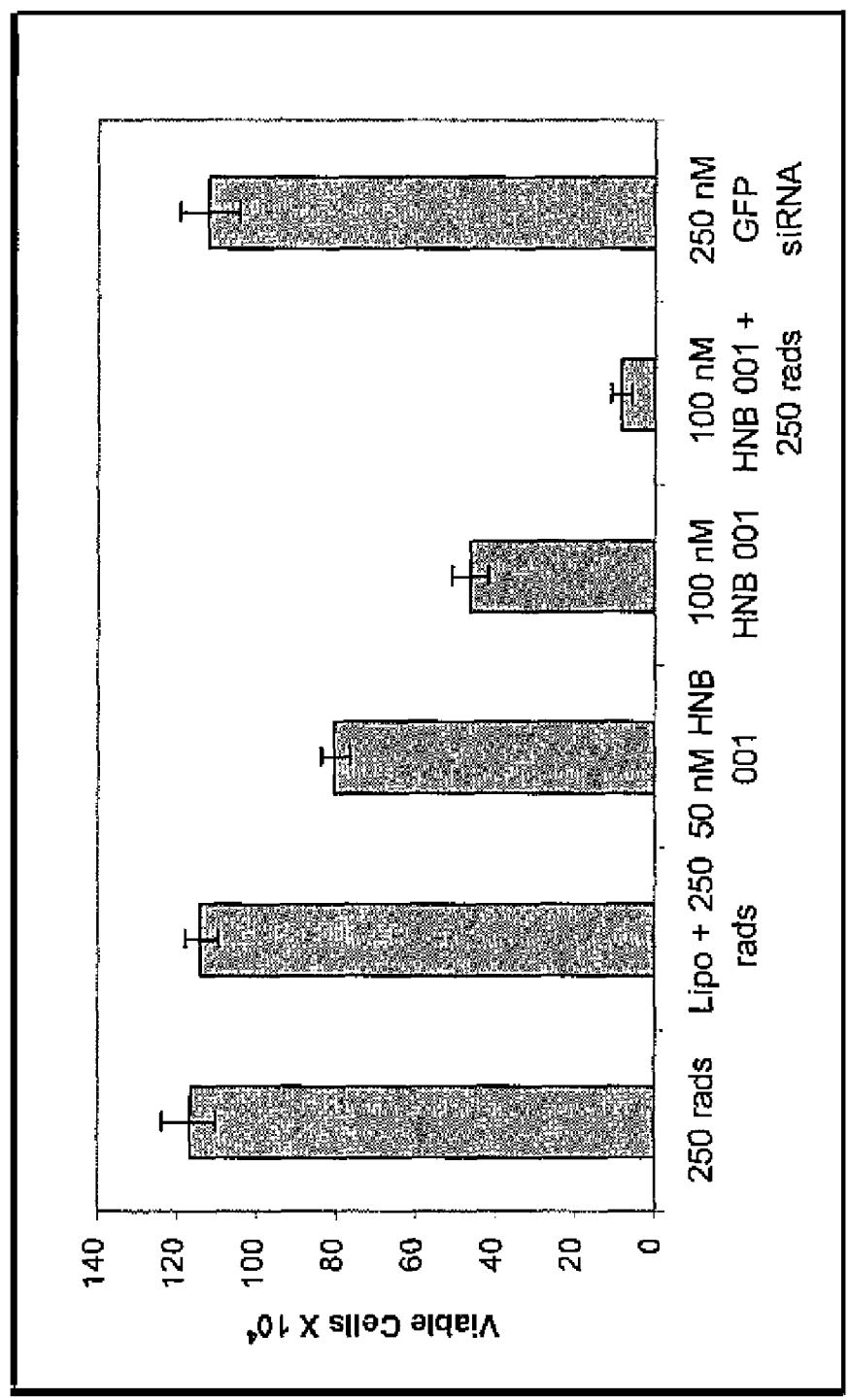
FIG. 8. Graph of viable MCF-7 cells as a function of siRNA concentration and/or radiation dosage.

The MCF-7 cell line, which is derived from estrogen sensitive human breast cancer, was used to demonstrate the effect of radiation on siRNA (50 and 100 nM HNB-001) transfected cells. Radiation had no effect on the viability of the control cells (radiation only, irradiated lipofectamine transfected, and 250 nM GFP siRNA transfected cells) (FIG. 8). In contrast, at siRNA concentrations of 50 nM and 100 nM, MCF-7 cell viability was decreased by about 22% and 50% respectively. Surprisingly, irradiated cells transfected with 100 nM siRNA displayed a decrease in cell viability of about 90%.

Example 8

Viability of siRNA Transfected PC-3 Cells Exposed to Radiation

Figure 9:
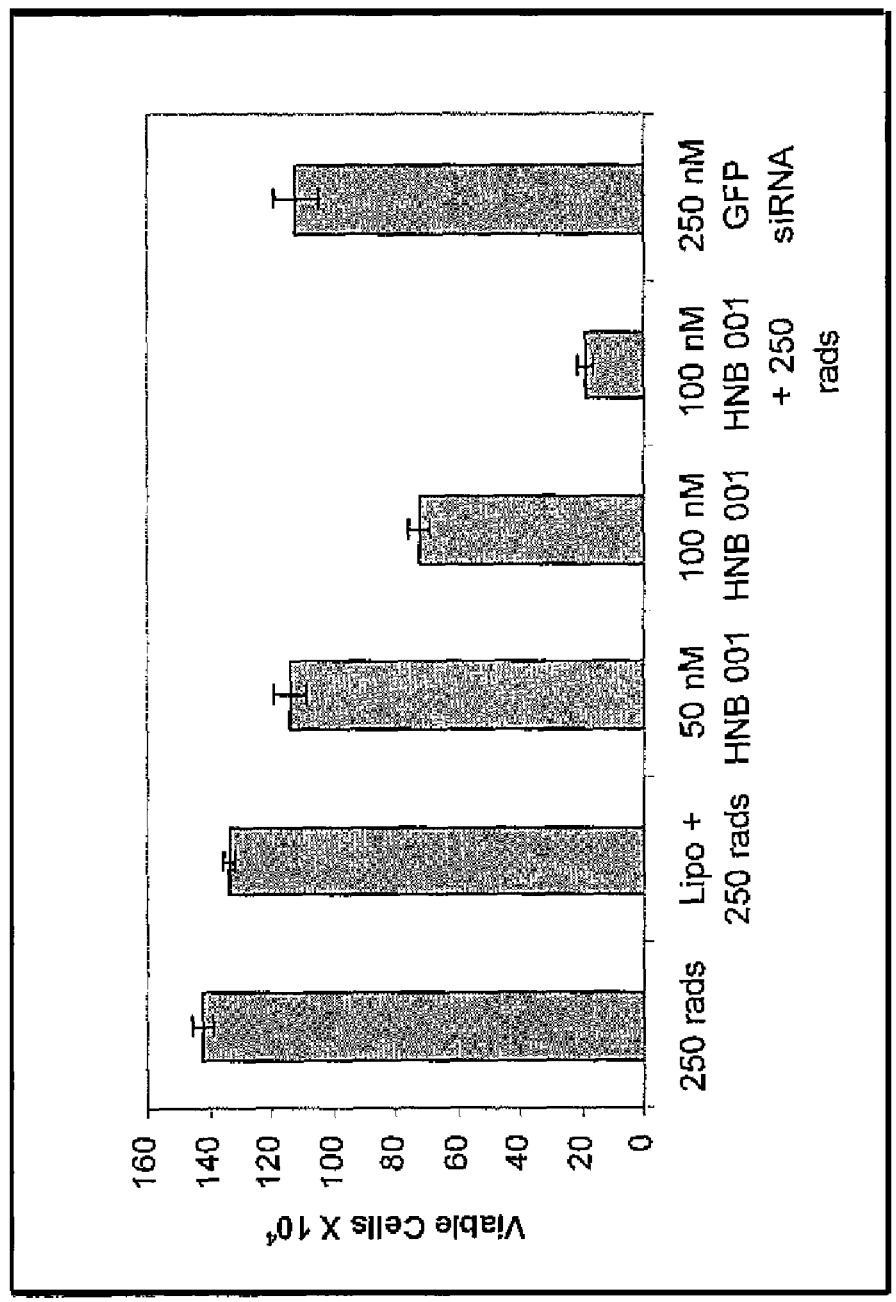
FIG. 9. Graph of viable PC-3 cells as a function of siRNA concentration and/or radiation dosage.

The PC-3 cell line, which is derived from human prostate cancer, was used to demonstrate the effect of radiation on siRNA (50 and 100 nM HNB-001) transfected cells. Radiation had no effect on the viability of the control cells (radiation only, lipofectamine transfected, and 250 nM GFP siRNA transfected cells) (FIG. 9). Whereas, cell viability was decreased by about 20% and 50% for 50 nM and 100 nM siRNA transfected cells respectively. In contrast, cell viability was decreased by about 85% in irradiated siRNA transfected cells.

Example 9

Viability of siRNA Transfected HT-29 Cells Exposed to Radiation

Figure 10:
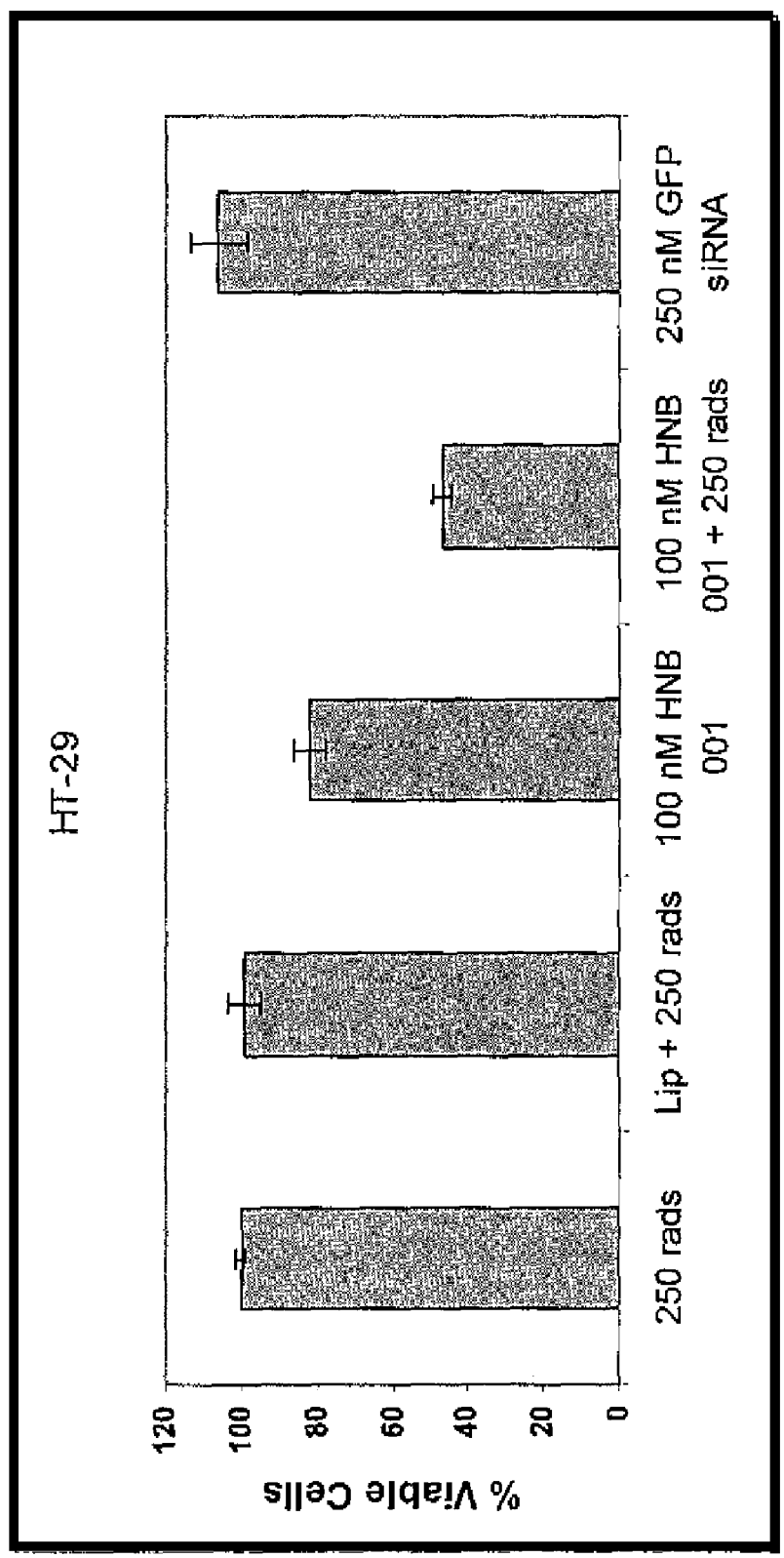
FIG. 10. Graph of viable HT-29 cells as a function of siRNA concentration and/or radiation dosage.

The HT-29 cell line which is derived from colon carcinoma, was used to demonstrate the effect of radiation on transfected siRNA (100 nM HNB-001). Radiation had no effect on the viability of the control cells (radiation only, lipofectamine transfected, and 250 nM GFP siRNA transfected cells) (FIG. 10). Decreases of about 20% in cell viability was observed for cells transfected with siRNA. Cell viability was decreased by about 50% in irradiated siRNA transfected cells.

Example 10

Effect of siRNA on Tumor Size with and without Radiation

In vivo experiments were performed in mice to determine whether the radiation potentiating effects displayed by the various cell lines exemplified above (Examples 5-9) would occur in tumor bearing mice (Balb/C, athymic).

SCC-15 cells were transfected with either 50 nM HNB-001 siRNA or 250 nM GFP siRNA using Lipofectamine™ 2000 according to the manufactures instructions. Forty-eight hours after transfection, cells were counted using trypan blue staining. Two million viable cells were injected subcutaneously into mice. The mice were divided into 4 groups: Groups I and II, consisted of GFP siRNA transfected cells and groups III and IV consisted of HNB-001 siRNA transfected cells. Mice in groups II and IV were irradiated at dose of 100 rad twice a week. The tumors were allowed to grow for 8 days and were measured on day 9 through day 18 using Digital calipers. The tumor volume was calculated using formula: a×b2 (squared)× 0.52 (22).

Figure 11:
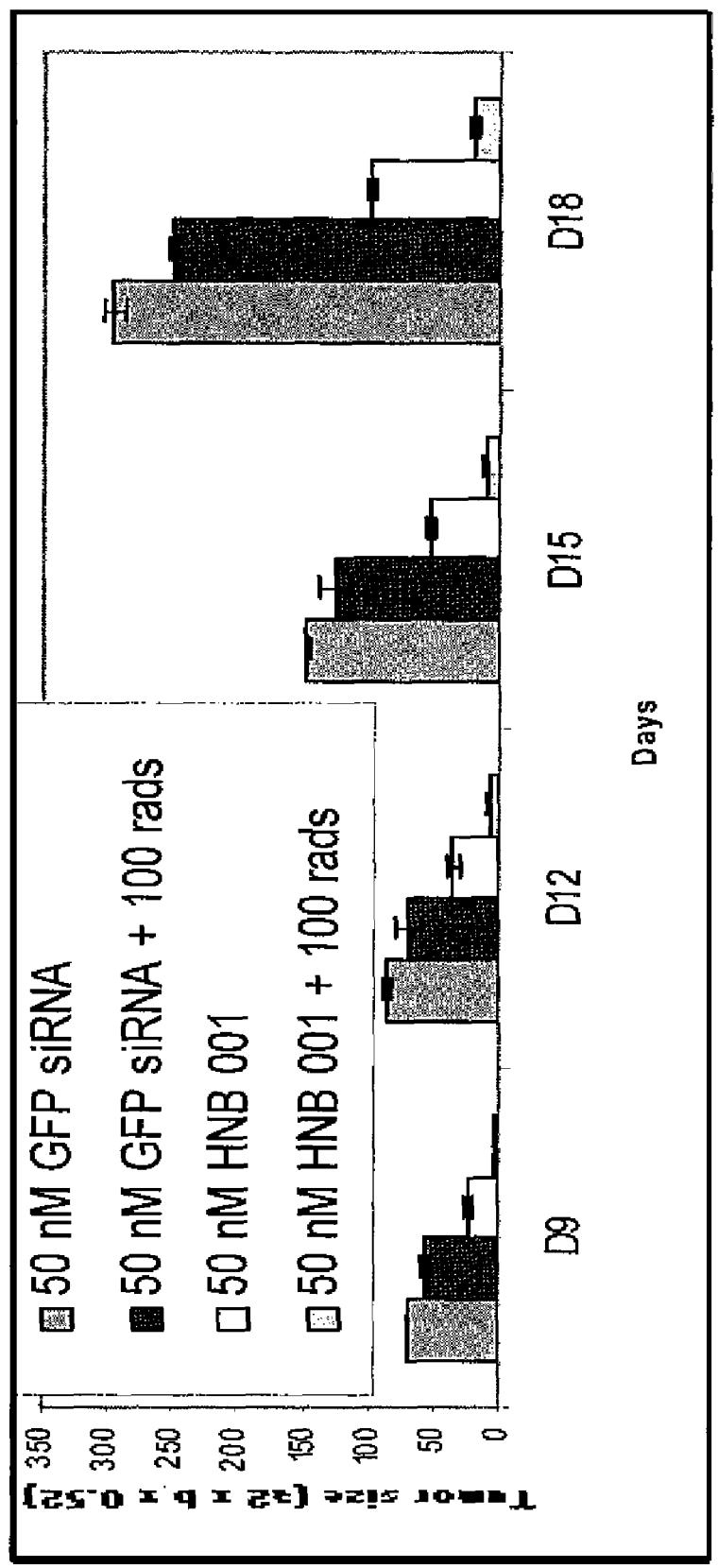
FIG. 11. Graph of tumor size as function of siRNA concentration and/or radiation dosage.
Figure 12:
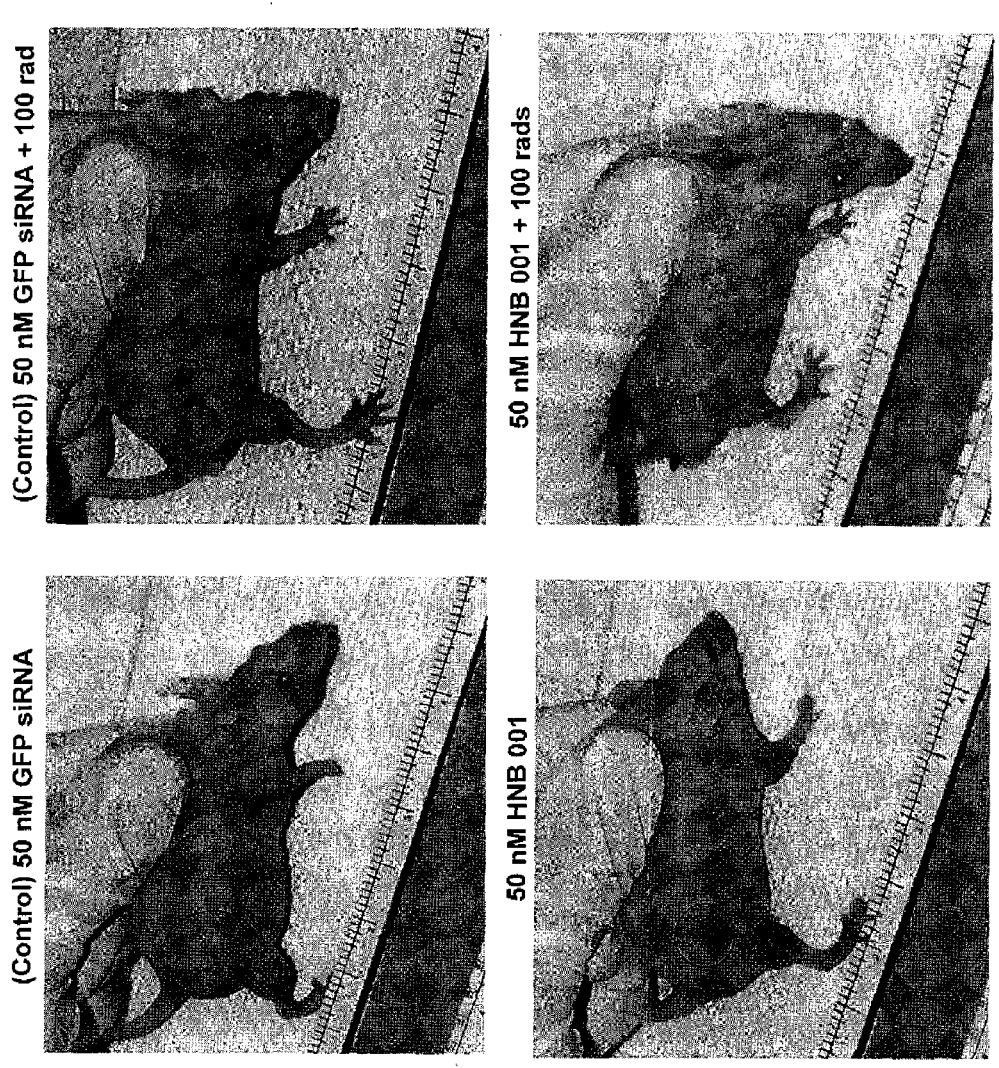
FIG. 12. Photograph of tumor size in mice treated with siRNA and/or radiation.

By day 18, the tumors in group 1 had grown 285 times in volume from when first measured on day 9 (FIG. 11). The tumors in group II had increased 250 times in size, group III tumors had increased 60 times in volume, and group IV tumors only increased 20 times in volume. Accordingly, more than 90% of tumor growth was inhibited by treatment with 50 nM of siRNA (HNB-001) and 100 rads of radiation (FIGS. 11 and 12). Therefore, the same radiation potentiating effects that occur in various cell lines, also occurred in mice.

Obviously, many modifications and variation of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

1. Visentin B, Vekich J A, Sibbald B J, Cavalli A L, Moreno K M, Matted R G, Garland W A, Lu Y, Yu 5, Hall H S, Kundra V, Mills G B, Sabbadini R A. Validation of an anti-sphingosine-1-phosphate antibody as a potential therapeutic in reducing growth, invasion, and angiogenesis in multiple tumor lineages. Cancer Cell. 2006; 9:225-38
2. Evan G I, Vousden K H. Proliferation, cell cycle and apoptosis in cancer. Nature. 2001; 411:342-348.
3. Shu X, Wu W, Mosteller R D, Broek D. Sphingosine kinase mediates vascular endothelial growth factor-induced activation of ras and mitogen-activated protein kinases. Mole. Cell. Bio. 2002; 22:77587768
4. Sankaranarayanan, R., Masuyer, E., Swaminathan, R., Ferlay, J., & Whelan S. Head and neck cancer: a global perspective on epidemiology and prognosis. Anticancer Res. 1998; 18: 4779-4786.
5. Brachman DG. Molecular biology of head and neck cancer. Semin Oncol. 1994; 21:320-329.
6. Doll F, Pfeilschifter J, Huwiler A. The epidermal growth factor stimulates sphingosine kinase-1 expression and activity in the human mammary carcinoma cell line MCF7. Biochim Biophys Acta. 2005; 1738:72-81.
7. Sarkar S, Maceyka M, Hait N C, Paugh S W, Sankala H, Milstien S, Spiegel S. Sphingosine kinase 1 is required for migration, proliferation and survival of MCF-7 human breast cancer cells. FEBS Lett. 2005; 579:5313-7.
8. Nava V E, Hobson J P, Murthy S, Milstien 5, Spiegel S. Sphingosine kinase type 1 promotes estrogen-dependent tumorigenesis of breast cancer MCF-7 cells. Exp Cell Res. 2002; 281:115-27
9. Kohno M, Momoi M, Oo M L, Paik J H, Lee Y M, Venkataraman K, Ai Y, Ristimaki A P, Fyrst H, Sano H, Rosenberg D, Saba J D, Proia R L, Hla T. Intracellular role for sphingosine kinase 1 in intestinal adenoma cell proliferation. Mol Cell Biol. 2006; 26: 7211-23.
10. Pchejetski D, Golzio M, Bonhoure E, Calvet C, Doumerc N, Garcia V, Mazerolles C, Rischmann P, Teissie J, Malavaud B, Cuvillier O. Sphingosine kinase-1 as a chemotherapy sensor in prostate adenocarcinoma cell and mouse models. Cancer Res. 2005; 65:11667-75.
11. Kawamori T, Osta W, Johnson K R, Pettus B J, Bielawski J, Tanaka T, Wargovich M J, Reddy B S, Hannun Y A, Obeid L M, Zhou D. Sphingosine kinase 1 is up-regulated in colon carcinogenesis. FASEB J. 2006; 20:386-8.
12. Johnson K R, Johnson K Y, Crellin H G, Ogretmen B, Boylan A M, Harley R A, Obeid L M. Immunohistochemical distribution of sphingosine kinase 1 in normal and tumor lung tissue. J Histochem Cytochem. 2005; 53:1159-66.
13. Le Scolan E, Pchejetski D, Banno Y, Denis N, Mayeux P, Vainchenker W, Levade T, Moreau-Gachelin F. Overexpression of sphingosine kinase 1 is an oncogenic event in erythroleukemic progression. Blood. 2005; 106:1808-16.
14. Mosteller R D, Broek D. VEGF receptor expression and signaling in human bladder tumors. Oncogene. 2003; 22:3361-70
15. French K J, Schrecengost R S, Lee B D, Zhuang Y, Smith S N, Eberly J L, Yun J K, Smith C D. Discovery and evaluation of inhibitors of human sphingosine kinase. Cancer Res. 2003; 63:5962-9.
16. Gamble J R, Xia P, Hahn C N, Drew J J, Drogemuller C J, Brown D, Vadas M A. Phenoxodiol, an experimental anticancer drug, shows potent antiangiogenic properties in addition to its antitumour effects. Int J. Cancer. 2006; 118: 2412-20.
17. Kim J W, Kim Y W, Inagaki Y, Hwang Y A, Mitsutake S, Ryu Y W, Lee W K, Ha H J, Park C S, Igarashi Y. Synthesis and evaluation of sphingoid analogs as inhibitors of sphingosine kinases. Bioorg Med Chem. 2005; 13:3475-85
18. Edsall L C, Van Brooklyn J R, Cuvillier O, Kleuser B, Spiegel S. N,N-Dimethylsphingosine is a potent competitive inhibitor of sphingosine kinase but not of protein kinase C: modulation of cellular levels of sphingosine 1-phosphate and ceramide. Biochemistry. 1998; 37:12892-8
19. Kono K, Tanaka M, Ogita T, Kohama T. Characterization of B-5354c, a new sphingosine kinase inhibitor, produced by a marine bacterium. J Antibiot (Tokyo). 2000; 53:759-64
20. Kano K, Tanaka M, Ogita T, Hosoya T, Kohama T. F-12509A, a new sphingosine kinase inhibitor, produced by a discomycete. J Antibiot (Tokyo). 2000; 53:459-66.
21. Atkins D, Reiffen K A, Tegtmeier C L, Whither H, Bonato M S, Storkel S. Immunohistochemical detection of EGFR in paraffin-embedded tumor tissues: variation in staining intensity due to choice of fixative and storage time of tissue sections. J Histochem Cytochem. 2004; 52:893-901.

22. Masood R, Kumar S R, Sinha U K, Crowe D L, Krasnoperov V, Reddy R K, Zozulya S, Singh J, Xia G, Broek D, Sehönthal A H, Gill P S. EphB4 provides survival advantage to squamous cell carcinoma of the head and neck. Int J. Cancer. 2006 Sep. 15; 119(6):1236-48.

23. Nava V E, Cuvillier O, Edsall L C, Kimura K, Milstien S, Gelmann E P, Spiegel S. Sphingosine enhances apoptosis of radiation-resistant prostate cancer cells. Cancer Res. 2000 Aug. 15; 60(16):4468-74.

What is claimed is:

1. A method of treating cancer in a subject comprising:
   administering to cancer cells in said subject a siRNA inhibitor in an amount sufficient to block the expression of sphingosine kinase 1 (SPK1) in the cancer cells and potentiate an effect of radiation, wherein the siRNA comprises a sense sequence and an antisense sequence, and the antisense sequence is complementary to an mRNA encoding SPK1, and
   administering radiation to the subject in an amount greater than or equal to 100 rads and less than or equal to 250 rads at a time when the effect of the radiation is potentiated by blocking expression of SPK1.

2. The method of claim 1, wherein the siRNA is double stranded and comprises a sense sequence comprising SEQ ID NO: 1 and an antisense sequence comprising SEQ ID NO: 2.

3. The method of claim 1, wherein the siRNA is double stranded and comprises a sense sequence comprising SEQ ID NO: 3 and an antisense sequence comprising SEQ ID NO: 4.

4. The method of claim 1, wherein the siRNA comprises 19-25 nucleotides.

5. The method of claim 1, wherein the cancer is breast, prostate, colorectal, lung, bladder, head and neck, intestine, ovarian, or skin cancer.

6. The method of claim 1, wherein the siRNA inhibitor is effective at blocking expression and potentiating the effect of radiation in least two or more different kinds of the cancer.

7. The method of claim 1, wherein the subject is a mammal.

8. The method of claim 1, further comprising periodically re-administrating the radiation.

9. The method of claim 8, where the radiation is periodically administered at a rate of at least twice per week.

10. The method of claim 5, wherein the cancer is head and/or neck cancer.

11. A method of treating head and/or neck cancer in a subject, comprising:
    administering to head and/or neck cancer cells in a subject a siRNA inhibitor in an amount sufficient to block the expression of sphingosine kinase 1 (SPK1) in the cancer cells and potentiate an effect of radiation, wherein the siRNA comprises a sense sequence and an antisense sequence, and the antisense sequence is complementary to an mRNA encoding SPK1, and
    administering radiation to the subject in an amount greater than or equal to 100 rads and less than or equal to 250 rads at a time when the effect of the radiation is potentiated by blocking expression of SPK1.

12. The method of claim 11, wherein the siRNA is double stranded and comprises a sense sequence comprising SEQ ID NO: 1 and an antisense sequence comprising SEQ ID NO: 2.

13. The method of claim 11, wherein the siRNA is double stranded and comprises a sense sequence comprising SEQ ID NO: 3 and an antisense sequence comprising SEQ ID NO: 4.

14. The method of claim 11, wherein the siRNA comprises 19-25 nucleotides.

15. The method of claim 11, further comprising periodically re-administrating the radiation.

16. The method of claim 15, where the radiation is periodically administered at a rate of at least twice per week.

* * * * *

```
                              SEQUENCE LISTING

<160> NUMBER OF SEQ ID NOS: 18

<210> SEQ ID NO 1
<211> LENGTH: 21
<212> TYPE: DNA
<213> ORGANISM: Artificial
<220> FEATURE:
<223> OTHER INFORMATION: Inhibitor Sequence

<400> SEQUENCE: 1
gggcaaggcu cugcagcuct t                                                    21

<210> SEQ ID NO 2
<211> LENGTH: 21
<212> TYPE: DNA
<213> ORGANISM: Artificial
<220> FEATURE:
<223> OTHER INFORMATION: Inhibitor sequence

<400> SEQUENCE: 2
gagcugcaga gccuugccct t                                                    21

<210> SEQ ID NO 3
<211> LENGTH: 21
<212> TYPE: DNA
<213> ORGANISM: Artificial
<220> FEATURE:
<223> OTHER INFORMATION: Inhibitor sequence

<400> SEQUENCE: 3
gggcaaggcc uugcagcuct t                                                    21

<210> SEQ ID NO 4
<211> LENGTH: 21
<212> TYPE: DNA
<213> ORGANISM: Artificial
<220> FEATURE:
<223> OTHER INFORMATION: Inhibitor sequence

<400> SEQUENCE: 4
gagcugcaag gccuugccct t                                                    21

<210> SEQ ID NO 5
<211> LENGTH: 21
<212> TYPE: DNA
<213> ORGANISM: Artificial
<220> FEATURE:
<223> OTHER INFORMATION: Inhibitor sequence

<400> SEQUENCE: 5
gagctgcaag gccttgccct t                                                    21

<210> SEQ ID NO 6
<211> LENGTH: 21
<212> TYPE: DNA
<213> ORGANISM: Artificial
<220> FEATURE:
<223> OTHER INFORMATION: Inhibitor sequence

<400> SEQUENCE: 6
```
aggccgctcc atgagcccgt t                                              21

<210> SEQ ID NO 7
<211> LENGTH: 21
<212> TYPE: DNA
<213> ORGANISM: Artificial
<220> FEATURE:
<223> OTHER INFORMATION: Inhibitor sequence

<400> SEQUENCE: 7
gttggtcagg aggtcttcat t                                              21

<210> SEQ ID NO 8
<211> LENGTH: 21
<212> TYPE: DNA
<213> ORGANISM: Artificial
<220> FEATURE:
<223> OTHER INFORMATION: Inhibitor sequence

<400> SEQUENCE: 8
ggtgtcttgg aacccactct t                                              21

<210> SEQ ID NO 9
<211> LENGTH: 21
<212> TYPE: DNA
<213> ORGANISM: Artificial
<220> FEATURE:
<223> OTHER INFORMATION: Inhibitor sequence

<400> SEQUENCE: 9
atactccata tgcctgccct t                                              21

<210> SEQ ID NO 10
<211> LENGTH: 21
<212> TYPE: DNA
<213> ORGANISM: Artificial
<220> FEATURE:
<223> OTHER INFORMATION: Inhibitor sequence

<400> SEQUENCE: 10
cggcctcgct aaccatcaat t                                              21

<210> SEQ ID NO 11
<211> LENGTH: 21
<212> TYPE: DNA
<213> ORGANISM: Artificial
<220> FEATURE:
<223> OTHER INFORMATION: Inhibitor sequence

<400> SEQUENCE: 11
gagctgcaga gccttgccct t                                              21

<210> SEQ ID NO 12
<211> LENGTH: 21
<212> TYPE: DNA
<213> ORGANISM: Artificial
<220> FEATURE:
<223> OTHER INFORMATION: Inhibitor sequence

<400> SEQUENCE: 12
tccgttcggt gagtatcagt t                                              21

<210> SEQ ID NO 13
<211> LENGTH: 21
<212> TYPE: DNA
<213> ORGANISM: Artificial

```
<220> FEATURE:
<223> OTHER INFORMATION: Inhibitor sequence

<400> SEQUENCE: 13
caccagctcc ctggcatggt t                                              21

<210> SEQ ID NO 14
<211> LENGTH: 21
<212> TYPE: DNA
<213> ORGANISM: Artificial
<220> FEATURE:
<223> OTHER INFORMATION: Inhibitor sequence

<400> SEQUENCE: 14
gttgatgagc aggtcttcat t                                              21

<210> SEQ ID NO 15
<211> LENGTH: 21
<212> TYPE: DNA
<213> ORGANISM: Artificial
<220> FEATURE:
<223> OTHER INFORMATION: Inhibitor sequence

<400> SEQUENCE: 15
gcacaacagc agtgtgcagt t                                              21

<210> SEQ ID NO 16
<211> LENGTH: 21
<212> TYPE: DNA
<213> ORGANISM: Artificial
<220> FEATURE:
<223> OTHER INFORMATION: Inhibitor sequence

<400> SEQUENCE: 16
ccaggtatgg acagtcaagt t                                              21

<210> SEQ ID NO 17
<211> LENGTH: 23
<212> TYPE: DNA
<213> ORGANISM: Artificial
<220> FEATURE:
<223> OTHER INFORMATION: Inhibitor sequence
<220> FEATURE:
<221> NAME/KEY: misc_feature
<222> LOCATION: (22)..(23)
<223> OTHER INFORMATION: n is a, c, g, t or u

<400> SEQUENCE: 17
cggccacaag uucagcgugu cnn                                            23

<210> SEQ ID NO 18
<211> LENGTH: 23
<212> TYPE: DNA
<213> ORGANISM: Artificial
<220> FEATURE:
<223> OTHER INFORMATION: Inhibitor sequence
<220> FEATURE:
<221> NAME/KEY: misc_feature
<222> LOCATION: (22)..(23)
<223> OTHER INFORMATION: n is a, c, g, t or u

<400> SEQUENCE: 18
gacacgcuga acuuguggcc gnn                                            23
```